(12) United States Patent
Ikarashi et al.

(10) Patent No.: US 8,268,578 B2
(45) Date of Patent: Sep. 18, 2012

(54) METHOD OF BIOASSAYING YOKUKANSAN

(75) Inventors: Yasushi Ikarashi, Inashiki-gun (JP); Zenji Kawakami, Inashiki-gun (JP)

(73) Assignee: Tsumura & Co., Tokyo (JP)

( * ) Notice: Subject to any disclaimer, the term of this patent is extended or adjusted under 35 U.S.C. 154(b) by 195 days.

(21) Appl. No.: 12/668,519

(22) PCT Filed: Jun. 27, 2008

(86) PCT No.: PCT/JP2008/061705
§ 371 (c)(1), (2), (4) Date: Jan. 11, 2010

(87) PCT Pub. No.: WO2009/008266
PCT Pub. Date: Jan. 15, 2009

(65) Prior Publication Data
US 2010/0196944 A1    Aug. 5, 2010

(30) Foreign Application Priority Data

Jul. 11, 2007   (JP) ................... 2007-181842

(51) Int. Cl.
*C12Q 1/02* (2006.01)
*C12P 21/06* (2006.01)
*C07K 1/00* (2006.01)

(52) U.S. Cl. .......... 435/29; 435/69.1; 530/350

(58) Field of Classification Search ............ 435/29, 435/69.1; 530/350
See application file for complete search history.

(56) References Cited

U.S. PATENT DOCUMENTS
2009/0098228 A1    4/2009  Ikarashi et al.

FOREIGN PATENT DOCUMENTS

| | | |
|---|---|---|
| JP | 11 174053 | 7/1999 |
| JP | 2000 512621 | 9/2000 |
| JP | 2001 521876 | 11/2001 |
| JP | 2005 520486 | 7/2005 |
| WO | 2005 121777 | 12/2005 |

OTHER PUBLICATIONS

U.S. Appl. No. 13/000,029, filed Dec. 20, 2010, Ikarashi, et al.
Kobayashi, Yoko et al., "Efflux of L-Glutamine and L-Serine from Rat Astrocytes after Exposure of L-Glutamic acid", Reports of the Research Committee of Essential Amino Acids, No. 176, pp. 77 to 82, (2006).
Arai, Hiroyuki et al., "Dementia with Lewy bodies", Dementia Japan, vol. 21, No. 1, pp. 81 to 88, Apr. 15, 2007.
U.S. Appl. No. 12/539,153, filed Aug. 11, 2009, Tohyama, et al.
U.S. Appl. No. 12/867,514, filed Aug. 13, 2010, Ikarashi, et al.
U.S. Appl. No. 12/936,282, filed Oct. 4, 2010, Ikarashi, et al.
US 5,637,563, 06/1997, Khwaja (withdrawn)

*Primary Examiner* — Karen Cochrane Carlson
*Assistant Examiner* — Natalie Moss
(74) *Attorney, Agent, or Firm* — Oblon, Spivak, McClelland, Maier & Neustadt, L.L.P.

(57) ABSTRACT

To find out an in-vitro bioassay system capable of ensuring qualities of yokukansan to a higher degree, it is intended to provide a method of bioassaying yokukansan characterized by comprising adding a yokukansan-containing test sample to astroglial cells to be cultivated under the condition of thiamine deficiency, and then determining the pharmacological activity value of yokukansan based on the glutamic acid or neutral red intake level in the cultivated astroglial cells.

9 Claims, 6 Drawing Sheets

METHOD OF BIOASSAYING YOKUKANSAN

CROSS-REFERENCE TO RELATED APPLICATIONS

This application is a National Stage of PCT/JP08/061,705 filed Jun. 27, 2008 and claims the benefit of JP 2007-181842 filed Jul. 11, 2007.

TECHNICAL FIELD

The present invention relates to a method of bioassay of yokukansan, and more precisely, to an assay method capable of quantitatively determining the physiological activity level (pharmacological activity value) of yokukansan, a type of kampo preparation, by the use of cultivated astroglial cells.

BACKGROUND ART

A kampo preparation is a pharmaceutical prepared by blending crude drugs, in which all the active ingredients are not always specifically identified. In this, a single active ingredient alone could not exhibit its effect, but some active ingredients may compositely act with each other. For securing its quality, an assay method capable of totally evaluating the whole kampo preparation is said necessary (Patent Document 1, Patent Document 2).

The assay method includes a method of total evaluation by assaying the individual ingredients, and a bioassay method of evaluating the physiological activity by the use of a biological material. The bioassay includes an in-vivo test and an in-vitro test, but the in-vivo test has many limitations regarding the test facilities and test animals, the processing capability, etc., and there are some difficulties in applying the in-vivo test to quality evaluation of kampo preparations.

On the other hand, the in-vitro test system does not require any special facilities and may give stable test results within a short period of time. Therefore, it is desired to establish a bioassay method with this system. In fact, for myostatin, a bioassay method is reported (Patent Document 3). However, for a kampo preparation that comprises a combination of crude drugs each having plural active ingredients by themselves, a suitable bioassay system could not always be found out, and the establishment of the bioassay system is desired.

For example, yokukansan, a type of kampo preparation generally has a composition mentioned below, for which, however, a suitable bioassay system is not as yet found out. For securing high quality for yokukansan, the development of the bioassay system for yokukansan is desired.

TABLE 1

| Ingredients | Amount |
| --- | --- |
| JP *Atractylodes Lancea* Rhizome | 4.0 g |
| JP *Poria Sclerotium* | 4.0 g |
| JP *Cnidium* Rhizoma | 3.0 g |
| JP Japanese Angelica Root | 3.0 g |
| JP *Bupleurum* Root | 2.0 g |
| JP *Glycyrrhiza* | 1.5 g |
| JP *Uncaria* Hook | 3.0 g |

Patent Document 1: JP-T 2000-512621
Patent Document 2: JP-T 2001-521876
Patent Document 3: JP-T 2005-520486

DISCLOSURE OF THE INVENTION

Problems that the Invention is to Solve

Accordingly, the object of the present invention is to find out a bioassay system with an in-vitro test for yokukansan that secures higher quality of the kampo preparation.

Means for Solving the Problems

The present inventors made intensive studies on the effect of yokukansan, and as a result, they found that the kampo preparation may improve the glutamic acid and neutral red intake reduction owing to the thiamine deficiency in astroglial cells, and that its effect for the improvement depends on the dose of yokukansan. In addition, the inventors found that the intake reduction is correlated with the metabolism activity of mitochondria. Further, the inventors found that application of these findings may construct a bioassay method for yokukansan, and thus the present invention has been completed.

Specifically, the invention provides a bioassay method for yokukansan, comprising adding a yokukansan-containing test sample to astroglial cells to be cultivated under the condition of thiamine deficiency, and determining the pharmacological activity value of yokukansan from the glutamic acid or neutral red intake level in the cultivated astroglial cells.

The invention also provides a bioassay method for yokukansan, comprising adding a yokukansan-containing test sample to astroglial cells to be cultivated under the condition of thiamine deficiency, and determining the pharmacological activity value of yokukansan from the mitochondrial metabolism activity of the cultivated astroglial cells.

Effects of the Invention

According to the bioassay method of the invention, the physiological activity level (pharmacological activity value) of yokukansan may be determined stably and in a simplified manner in an in-vitro test with no limitation on the test facilities and test animals and on the processing capability, etc.

BEST MODE FOR CARRYING OUT THE INVENTION

The bioassay method for yokukansan of the present invention comprises adding a yokukansan-containing test sample to astroglial cells to be cultivated under the condition of thiamine deficiency, and after the addition, determining the pharmacological activity value of yokukansan from the glutamic acid or neutral red intake level or the mitochondrial metabolism activity of the cultivated astroglial cells.

The astroglial cells to be cultivated under the condition of thiamine deficiency that are used in the invention (hereinafter referred to as "thiamine-deficient astroglial cells" or "T-deficient astroglia") may be produced, for example, by culturing astroglial cells that are obtained according to a Juurlink & Hertz's method (Juurlink B J H, Hertz L (1992) Astrocytes. Boulton B A, Baker G B, Waltz W (eds). In: *Neuromethods*, page 269-321, The Humana Press Inc. Totowa, N.J.), for a predetermined period of time, for example, for from 7 days to 10 days, in a medium not containing thiamine.

In the thiamine-deficient astroglial cells thus prepared, the transporter function has lowered and the membrane function has been disordered; and as compared with that of normal astroglial cells, the glutamic acid and the like intake level has lowered.

One embodiment of the bioassay method of the present invention comprises culturing astroglial cells in a medium containing a yokukansan-containing test sample, under the condition of thiamine deficiency, then adding glutamic acid or neutral red thereto, further culturing the cells for a predetermined period of time, and thereafter measuring the amount of glutamic acid or neutral red in the culture. For glutamic acid, the period of time for cultivation may be from 1 to 7 hours, preferably 5 hours; and for neutral red, it may be from 1 to 5 hours, preferably 2 hours.

From the data, it is possible to quantitatively determine the pharmacological activity value that is generally recognized as the amount of yokukansan in the added test sample. The glutamic acid concentration or the neutral red amount after the cultivation is preferably measured by absorptiometric detection. In this case, the glutamic acid concentration is the glutamic acid amount in the culture having still remained as not taken by the cells, and the amount of neutral red is the amount of neutral red taken by the cells.

In the above measurement, in general, it is desirable that plural samples, preferably at least 3 samples each containing a known concentration of yokukansan are simultaneously analyzed, and the pharmacological activity value of yokukansan in these test samples is determined; however, so far as the condition does not almost differ, a calibration curve previously prepared from samples each containing a known concentration of yokukansan may be used for the determination.

Another embodiment of the bioassay method of the present invention comprises cultivating astroglial cells that have been cultivated under the condition of thiamine deficiency, in a medium containing a yokukansan-containing test sample for a predetermined period of time, and after the cultivation, measuring the mitochondrial metabolism activity of the astroglial cells, thereby determining the pharmacological activity value of yokukansan from the data.

One specific embodiment of this method comprises comparing the mitochondrial metabolism activity of the astroglial cells having been cultivated in a medium prepared by adding a yokukansan-containing test sample to a thiamine-deficient medium, with the mitochondrial metabolism activity of the astroglial cells having been cultivated in a thiamine-deficient medium not containing the yokukansan-containing test sample, thereby determining the pharmacological activity of yokukansan in the test sample.

In such a method, the mitochondrial metabolism activity may be measured, for example, through 3-(4,5-dimethylthiazol-2-yl)-2,5-diphenyltetrazolium bromide (MTT) reduction. Specifically, the mitochondrial metabolism activity may be determined by measuring formazane produced by MTT. Needless-to-say, any other known method capable of measuring mitochondrial metabolism activity may also be employed.

Also in this measurement, it is generally desirable that plural samples, preferably at least 3 samples each containing a known concentration of yokukansan are simultaneously analyzed, and the pharmacological activity value of yokukansan in these test samples is determined; however, so far as the condition does not almost differ, a calibration curve previously prepared from samples each containing a known concentration of yokukansan may be used for the determination.

As in the above, the pharmacological activity value of yokukansan in test samples may be evaluated, and this action mechanism is directly based on the action of yokukansan. Specifically, according to the present inventors' studies, it has been found that yokukansan may improve the membrane and the glutamic acid transporter function of astroglial cells. From the finding that yokukansan may improve the membrane and the transporter function of the cells, when thiamine-deficient astroglial cells of which the membrane and the transporter function have lowered are used, it has become possible to determine and evaluate the pharmacological activity value of yokukansan.

The mitochondrial metabolism activity is considered to be associated with the mechanism of glutamic acid or neutral red intake; and based on it, it is possible to determine and evaluate the pharmacological activity value of yokukansan. Specifically, when astroglial cells take glutamic acid or the like, they require energy, and the energy is produced by mitochondria; and therefore, there is a relation that, when the activity of the mitochondria lowers, then the activity of the cells to take glutamic acid and the like also lowers.

Further, according to the bioassay method of the present invention, a standard preparation clinically recognized to have a pharmacological effect as yokukansan and a test preparation are tested and evaluated for the pharmacological activity value under the same condition, and the standard preparation and the test preparation are compared with each other, whereby the quality equivalence of the preparation can be evaluated.

Furthermore, plural lots of preparations are tested and evaluated for the pharmacological activity value according to the bioassay method of the present invention, and based on the uppermost and lowermost ranges derived from the mean data, the pharmacological activity value of the test samples may be evaluated as to whether or not it falls within the ranges; and from this the quality equivalence of the tested preparations can be evaluated.

EXAMPLES

The present invention is described in more detail with reference to the following Examples. However, the invention should not be whatsoever restricted at all by these Examples.

Example 1

Glutamic Acid Intake Test (1) Cultivation of astroglial cells:

Astroglial cells were cultivated according to the Juurlink & Hertz's method. Concretely, a cerebral cortex was taken out from a newborn rat (1 day after birth), and using a 100-μm mesh, the cells were mechanically dissociated. The dissociated cells were filtered through a lens cleaning paper filter to remove the residue. The obtained cells were washed three times by centrifugation at 1,000 rpm for 10 minutes, then floated in a 10% equine serum-containing DMEM medium (cell growth medium), and inoculated in a flask in an amount of 50,000 cells/cm$^2$ (culture area ratio). After cultivated for one day in the cell growth medium, these were selectively cultivated for 2 weeks in a 10% dialytic equine serum-containing sorbitol-containing DMEM medium (not containing glucose). These were returned to the cell growth medium, thereby obtaining cultivated astroglial cells.

(2) The cultivated astroglial cells obtained in the manner as above were sowed in each well of a 96-well plate in a density of 20,000 cells/cm$^2$, and pre-cultivated for 1 week. Next, these were cultivated in a thiamine-deficient DMEM medium for 7 days, thereby obtaining thiamine-deficient cultivated astroglial cells. On the other hand, the cells were cultivated in a thiamin-containing DMEM medium for 7 days, thereby obtaining normal cultivated astroglial cells. To all the cells, 5% equine serum was added during the cultivation, and the medium was changed to a serum-free medium on the day before the test. The cells cultivated for 7 days in a yokukansan (TJ-54 by TSUMURA & Co., hereinafter referred to as "TJ-54")-added, thiamine-deficient DMEM medium are referred to as TJ-54-added thiamine-deficient cultivated astroglial cells.

(3) The test for the glutamic acid intake capability was as follows: First, to the normal astroglial cells, the thiamine-deficient cultivated astroglial cells and the TJ-54-added thiamine-deficient cultivated astroglial cells obtained in (2), added was a 100 μM glutamic acid-added serum-free medium. These are a normal control group, a thiamine-deficient group, and a TJ-54 group, respectively.

In 5 hours after the glutamic acid addition, a culture supernatant was collected from the samples of each group, and the glutamic acid concentration in the supernatant was measured, thereby determining and evaluating the glutamic acid intake capability of the cells. The glutamic acid concentration in the medium was measured according to an Abe K et al's method (Abe K., Abe Y., Saito H., (2000) Evaluation of L-glutamate clearance capacity of cultured rat cortical astrocytes., *Biol. Pharm. Bull.*, 23: 204-207). Briefly, 50 μl of a reaction solution was added to 50 μl of the culture supernatant to be analyzed, and reacted at 37° C. for 10 minutes, and then the reaction was stopped with 100 μl of a stopper liquid added thereto. Then, the absorbance of the sample was measured at a test wavelength of 540 nm (reference wavelength 690 nm). The results are shown in FIG. 1. In this graph, also shown are the data of the glutamic acid intake capability of the thiamine-deficient cultivated astroglial cells (comparison group), using a medium prepared by adding 100 μM of a glutamic acid transporter inhibitor, DL-threo-β-hydroxyaspartic acid (TBHA) and 500 μg/ml of TJ-54 to a 100 μM glutamic acid-added serum-free medium.

As is obvious from the results, it is shown that TJ-54 dose-dependently increased the glutamic acid intake by the thiamine-deficient cultivated astroglial cells, within a dose range of from 100 to 700 μg/ml. In addition, since the action of TJ-54 (500 μg) was antagonized by TBHA, it is suggested that the glutamic acid intake-improving action of TJ-54 is attained by the glutamic acid transporter. The intake increase (improvement) action by TJ-54 is shown as a calibration curve in FIG. 2.

Example 2

Neutral Red Intake Test

The normal cultivated astroglial cells, the thiamine-deficient cultivated astroglial cells and the TJ-54-added thiamine-deficient cultivated astroglial cells prepared in Example 1 (1) and (2) were used in a neutral red intake test. The medium was not changed to a serum-free medium on the day before the test.

Concretely, 100 μl of a neutral red solution (150 μg/ml) was added to 100 μl of the medium in a 96-well plate, and cultivated for 2 hours. Next, the culture was removed, then 200 μl of washing/fixation liquid was added and left as such for 1 minute. Further, the washing/fixation liquid was removed, and 100 μl of an extraction solvent was added and left as such for 20 minutes, whereby the neutral red taken by the cells was extracted out. Next, the plate was stirred, and the absorbance at 540 nm was measured, thereby quantitatively determining the neutral red intake. The results are shown in FIG. 3.

As is obvious from the results, it is shown that TJ-54 dose-dependently increased the neutral red intake within a dose range of from 10 to 500 μg/ml. This is shown as a calibration curve in FIG. 4.

Example 3

Mitochondrial Metabolism Activity Test (1) The normal cultivated astroglial cells, the thiamine-deficient cultivated astroglial cells and the TJ-54-added thiamine-deficient cultivated astroglial cells prepared in Example 1 (1) and (2) were used for mitochondrial metabolism activity determination. The medium was not changed to a serum-free medium on the day before the test.

On the day 7 after the addition of TJ-54, the mitochondrial metabolism activity with MTT was measured according to the method mentioned below. The results are shown in FIG. 5.
(Method for Measurement of Mitochondrial Metabolism Activity with MTT)

20 μl of an MTT liquid (5 mg/ml, in phosphoric buffer solution) was added to 100 μl of the medium in the 96-well plate, and the cells were cultivated at 37° C. for 5 hours. 100 μl of a stopper liquid (0.01 N HCl solution of 10% SDS) was added thereto to stop the reaction. The amount of formazane formed from MTT by the reaction was measured on the next day (after left overnight as such), using an absorptiometer (test wavelength: 570 nm, reference wavelength: 690 nm).

As shown in FIG. 5, the MTT activity of the astroglial cells significantly lowered in the thiamine-free medium. As opposed to this, TJ-54 significantly dose-dependently prevented the MTT activity reduction in the thiamine-free medium in a concentration of at least 250 μg/ml. This is shown as a calibration curve in FIG. 6.

From these results, it is shown that the pharmacological activity value of TJ-54 can be determined by reacting a TJ-54-containing sample with astroglial cells cultivated in a thiamine-free medium followed by analyzing the cells for the mitochondrial metabolism activity-improving effect thereof.

INDUSTRIAL APPLICABILITY

According to the present invention, the pharmacological activity value of yokukansan can be determined stably and in a simplified manner in an in-vitro test with no limitation on the test facilities and test animals and on the processing capability, etc.

Accordingly, as compared with a conventional method of analyzing a predetermined constitutive ingredient of yokukansan, the invention makes it possible to secure the quality of yokukansan to a higher degree.

Figure 1:
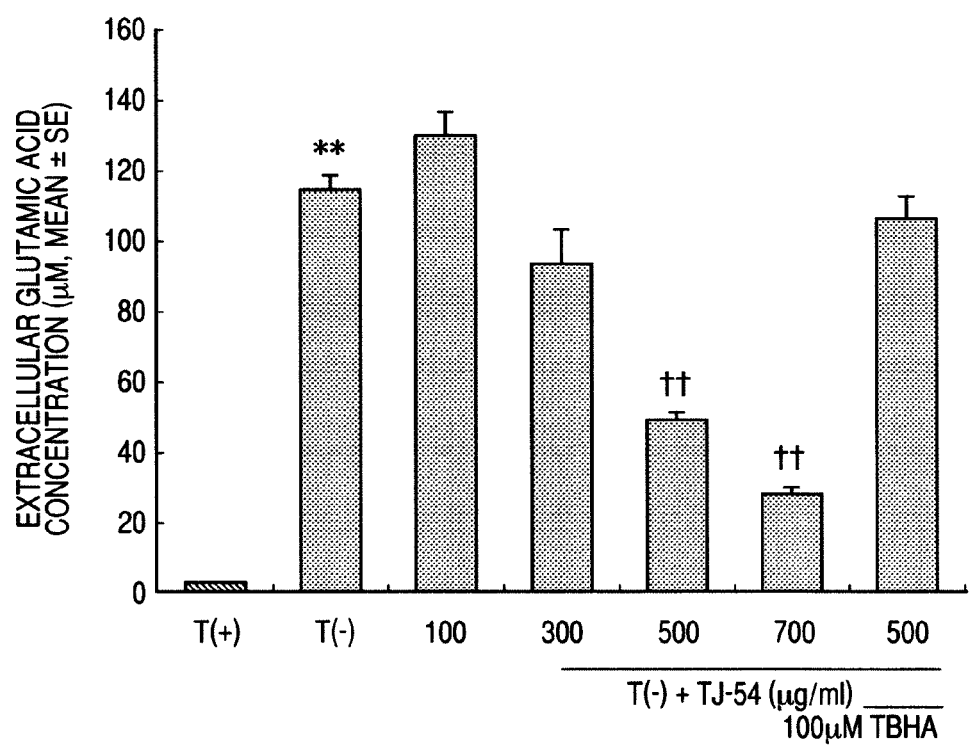
FIG. 1 shows the results of determination of glutamic acid intake performance. In this, T(+) indicates normal cultivated astroglial cells, and T(−) indicates thiamine-deficient cultivated astroglial cells.
Figure 2:
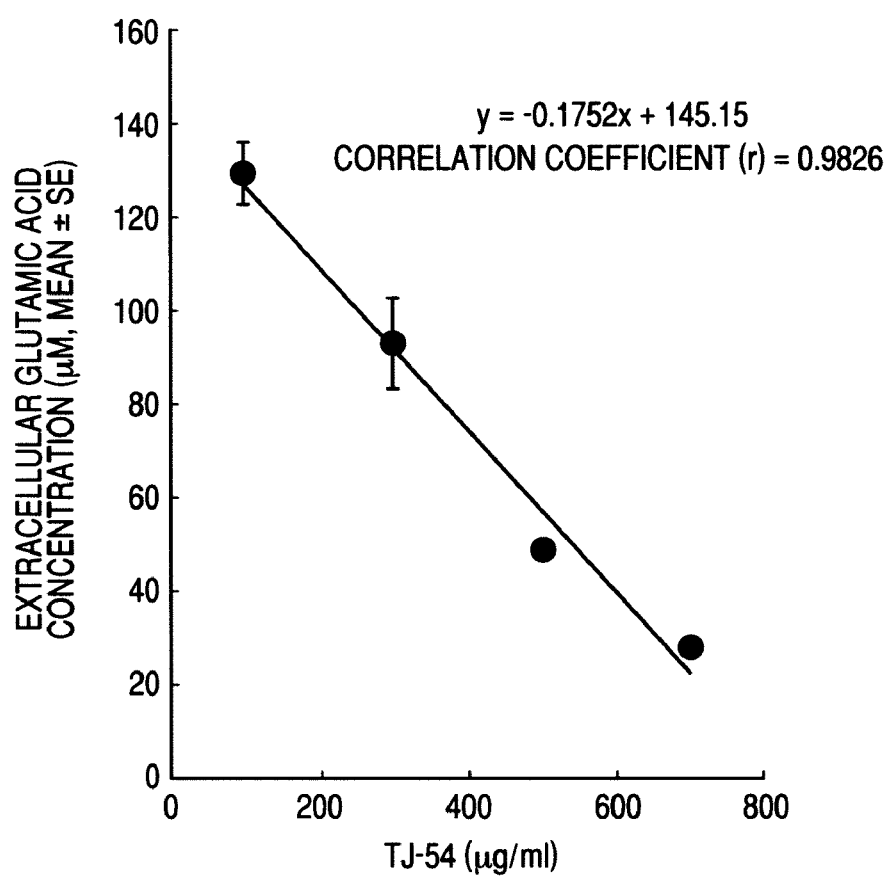
FIG. 2 shows a calibration curve formed from the results in the above FIG. 1.
Figure 3:
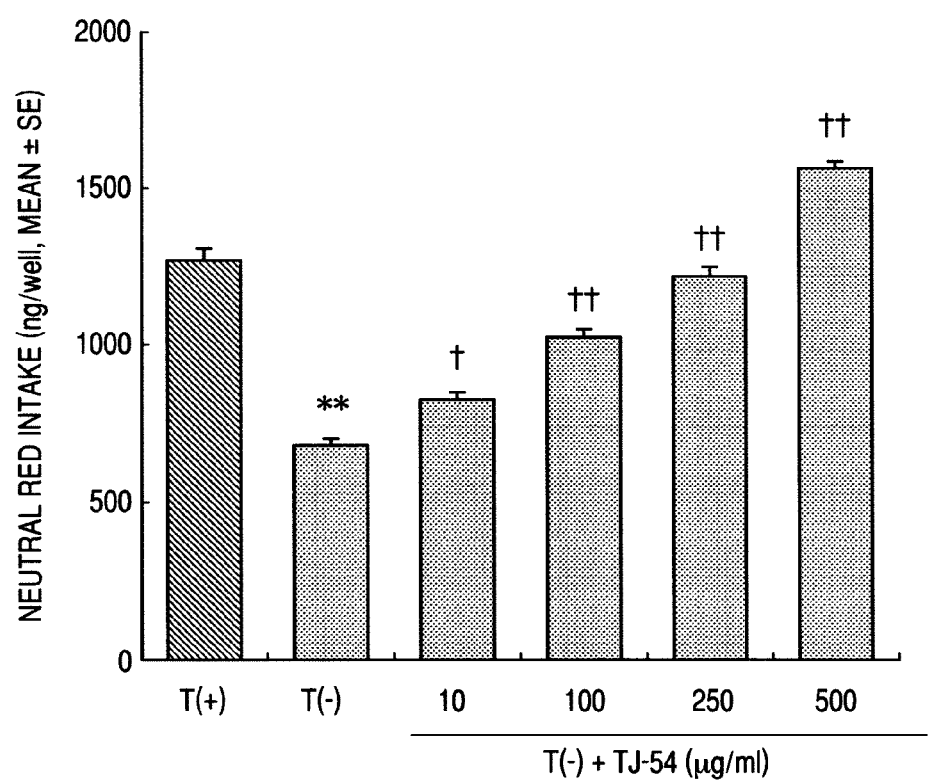
FIG. 3 shows the results of determination of neutral red intake performance. In this, T(+) and T(−) are the same as in FIG. 1.
Figure 4:
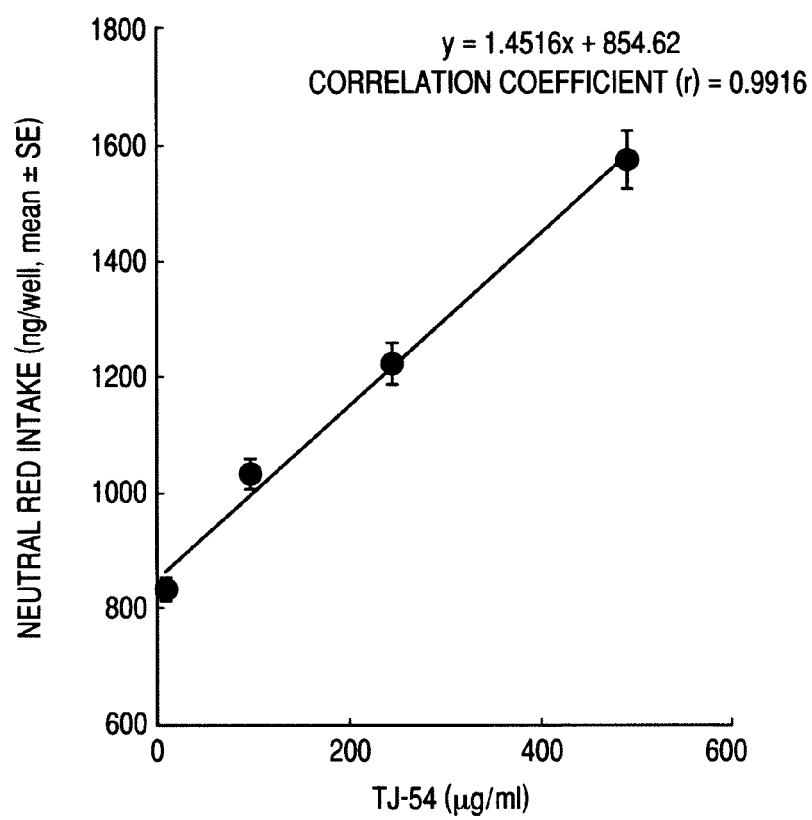
FIG. 4 shows a calibration curve formed from the results in the above FIG. 3.
Figure 5:
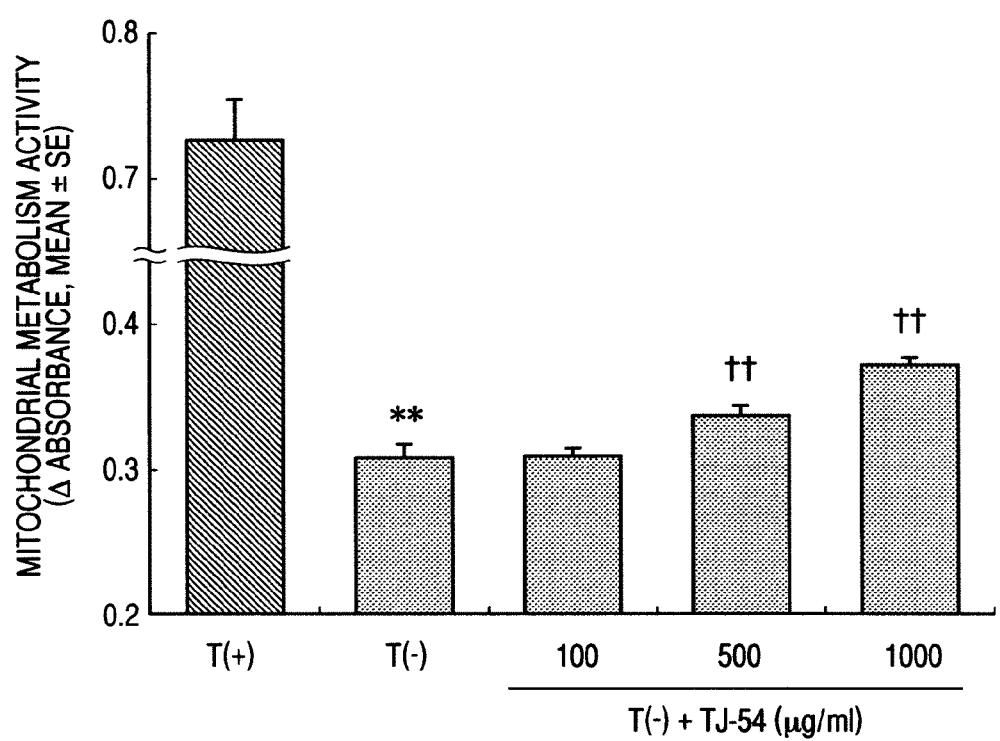
FIG. 5 shows the results of determination of mitochondrial metabolism activity. In this, T(+) and T(−) are the same as in FIG. 1.
Figure 6:
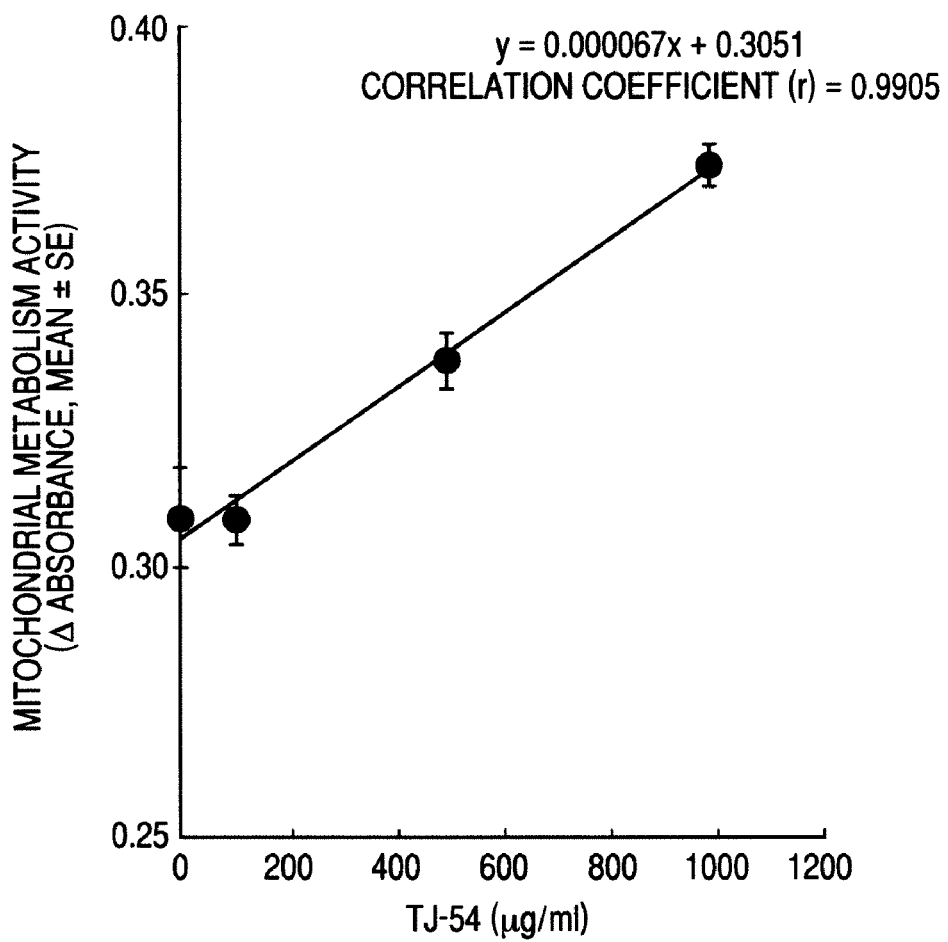
FIG. 6 shows a calibration curve formed from the results in the above FIG. 5.

The invention claimed is:

1. A method for determining the activity of yokukansan in a test sample, the method comprising
    adding a yokukansan-containing test sample to astroglial cells cultivated in a thiamine deficient culture medium,
    adding glutamic acid or neutral red to the culture medium, and
    measuring the glutamic acid or neutral red intake level in the cultivated astroglial cells and comparing the measured glutamic acid or neutral red intake level to a calibration curve that correlates known yokokansan activity to glutamic acid or neutral red intake levels in astroglial cells cultivated in a thiamine deficient culture medium to determine the activity of yokukansan in the test sample.

2. A method for quantitating yokukansan in a test sample, the method comprising
    adding a yokukansan-containing test sample to astroglial cells cultivated in a thiamine deficient culture medium,
    adding glutamic acid or neutral red to the culture medium, and
    measuring the glutamic acid or neutral red intake level in the cultivated astroglial cells and comparing the measured glutamic acid or neutral red intake level to a calibration curve that correlates known yokukansan concentrations to glutamic acid or neutral red intake levels in astroglial cells cultivated in a thiamine deficient culture medium to determine the concentration of yokukansan in the test sample.

3. A method for determining the activity of yokukansan in a test sample, the method comprising
    adding a yokukansan-containing test sample to astroglial cells cultivated in a thiamine deficient culture medium, and
    measuring the mitochondrial metabolism activity in the cultivated astroglial cells and comparing the measured mitochondrial metabolism activity to a calibration curve that correlates known yokokansan activity to mitochondrial metabolism activity in astroglial cells cultivated in a thiamine deficient culture medium to determine the activity of yokukansan in the test sample.

4. The method according to claim 3, wherein mitochondrial metabolism activity is measured by measuring 3-(4,5-dimethylthiazol-2-yl)-2,5-diphenyltetrazolium bromide (MTT) reduction in the cultivated astroglial cells to which the test sample or control sample is added.

5. The method according to claim 3, wherein the mitochondrial metabolism activity is measured by measuring formazane produced by MTT in the cultivated astroglial cells to which the test sample or control sample is added.

6. The method according to claim 1, wherein the glutamic acid intake level is measured and correlated.

7. The method according to claim 2, wherein the glutamic acid intake level is measured and correlated.

8. The method according to claim 1, wherein the neutral red intake level is measured and correlated.

9. The method according to claim 2, wherein the neutral red intake level is measured and correlated.

* * * * *